United States Patent
Ren et al.

(10) Patent No.: US 7,097,865 B2
(45) Date of Patent: Aug. 29, 2006

(54) INHIBITION OF CYP450 1A2, 2A6, 2C9, 2C19, 2D6, 2E1, AND 3A4 IN CRYOPRESERVED HUMAN HEPATOCYTES BY A TRIPTERYGIUM WILFORDII HOOK. F. EXTRACT

(75) Inventors: Keyong Ren, Denville, NJ (US); Xieyu Lu, Nanjing (CN); Xuhua Luo, Beijing (CN)

(73) Assignee: Novemed Group Limited, Beijing (CN)

( * ) Notice: Subject to any disclaimer, the term of this patent is extended or adjusted under 35 U.S.C. 154(b) by 332 days.

(21) Appl. No.: 10/776,433

(22) Filed: Feb. 11, 2004

(65) Prior Publication Data

US 2004/0161479 A1 Aug. 19, 2004

Related U.S. Application Data

(63) Continuation-in-part of application No. 10/236,139, filed on Sep. 6, 2002, now abandoned.

(51) Int. Cl.
*A01K 65/00* (2006.01)
(52) U.S. Cl. .................................... 424/725
(58) Field of Classification Search ................ 424/725
See application file for complete search history.

(56) References Cited

U.S. PATENT DOCUMENTS

| | | | | |
|---|---|---|---|---|
| 4,005,108 A | * | 1/1977 | Kupchan et al. | 549/297 |
| 5,192,817 A | * | 3/1993 | Takaishi et al. | 549/298 |
| 5,430,054 A | * | 7/1995 | Qian et al. | 514/468 |

OTHER PUBLICATIONS

Li et al., Cyopreserved human hepatocytes: characterization of drug-metabolizing enzyme activities and applications in higher throughput screening assays for hepatotoxicity, metabolic stability, and drug-drug interaction potential, *Chem. Biol. Interact.* 121, 17-35 (1999).

Li et al., Isolation and culturing of hepatocytes from human livers., *J. Tiss. Culture Methods* 14, 139-146 (1992).

Loretz et al., Optimization of cryopreservation procedures for rat and human hepatocytes., *Xenobiotica* 19(5), 489-498.

Ruegg et al, Cytochrome-P450 induction and conjugated metabolism in primary human hepatocytes after cryopreservation, *In Vitro Toxicol.* 10(2), 217-222 (1997).

* cited by examiner

*Primary Examiner*—Patricia Leith
(74) *Attorney, Agent, or Firm*—Cohen, Pontani, Lieberman & Pavane

(57) ABSTRACT

A method of inhibiting chytochrome P450 enzymes selected from the group consisting of CYP1A2, CYP2A6 and CYP3A4 comprises the step of administering an effective inhibition amount of AHT-323A botanical extract to a patient.

4 Claims, 3 Drawing Sheets

IC$_{50}$: 0.176 mg/mL
95% Confidence Intervals: 0.133-0.233 mg/mL
Goodness of Fit: 0.966

$IC_{50}$: 0.741 mg/mL
95% Confidence Intervals: 0.628-0.873 mg/mL
Goodness of Fit: 0.900

IC$_{50}$: 0.0366 mg/mL
95% Confidence Intervals: 0.0293-0.0457 mg/mL
Goodness of Fit: 0.990

INHIBITION OF CYP450 1A2, 2A6, 2C9, 2C19, 2D6, 2E1, AND 3A4 IN CRYOPRESERVED HUMAN HEPATOCYTES BY A TRIPTERYGIUM WILFORDII HOOK. F. EXTRACT

CROSS REFERENCE TO RELATED APPLICATIONS

This application is a continuation-in-part of U.S. patent application Ser. No. 10/236,139 which was filed with the U.S. Patent and Trademark Office on Sep. 6, 2002 now abandoned.

BACKGROUND OF THE INVENTION

1. Field of the Invention

The present invention relates to a method of inhibiting cytochrome P450 enzymes by administering a Tripterygium Wilfordii Hook. F. (TW) extract. More specifically, inhibitions of cytochrome P450 (CYP450) isoforms 1A2, 2A6, 2C9, 2C19, 2D6, 2E1, and 3A4 in cryopreserved human hepatocytes were studied. The method is particularly useful in determining drug-drug interactions when the TW extract is co-administered with other drugs.

2. Description of the Related Art

Cytochrome P-450 is a superfamily of enzymes that metabolize a large number of drugs, xenobiotics and endogenous substances in vitro and in vivo. Enzymes of the cytochrome P450 superfamily catalyze the oxidative metabolism of a variety of substrates, including natural compounds such as steroids, fatty acids, prostaglandins, leukotrienes, and vitamins, as well as drugs, carcinogens, mutagens, and xenobiotics. Cytochrome P450s, also known as P450 heme-thiolate proteins, usually act as terminal oxidases in multi-component electron transfer chains, called P450-containing monooxygenase systems. Specific reactions catalyzed include hydroxylation, epoxidation, N-oxidation, sulfooxidation, N-, S-, and O-dealkylations, desulfation, deamination, and reduction of azo, nitro, and N-oxide groups. These reactions are involved in steroidogenesis of glucocorticoids, cortisols, estrogens, and androgens in animals; insecticide resistance in insects; herbicide resistance and flower coloring in plants; and environmental bioremediation by microorganisms. Cytochrome P450 actions on drugs, carcinogens, mutagens, and xenobiotics can result in detoxification or in conversion of the substance to a more toxic product. Cytochrome P450s are abundant in the liver, but also occur in other tissues. Members of the cytochrome P450 family are present in varying levels and their expression and activities are controlled by variables such as chemical environment, sex, developmental stage, nutrition and age.

More than 200 cytochrome P450 genes have been identified. There are multiple forms of these P450 and each of the individual forms exhibit degrees of specificity towards individual chemicals in the above classes of compounds. In some cases, a substrate, whether a drug or a carcinogen, is metabolized by more then one of the cytochromes P450. All cytochrome P450s use a heme cofactor and share structural attributes. Most cytochrome P450s are 400 to 530 amino acids in length. The secondary structure of the enzyme is about 70% alpha-helical and about 22% beta-sheet.

Genetic polymorphisms of cytochromes P450 result in phenotypically-distinct subpopulations that differ in their ability to perform biotransformations of particular drugs and other chemical compounds. These phenotypic distinctions have important implications for selection of drugs. For example, a drug that is safe when administered to most humans may cause toxic side-effects in an individual suffering from a defect in an enzyme required for detoxification of the drug. Alternatively, a drug that is effective in most humans may be ineffective in a particular subpopulation because of lack of a enzyme required for conversion of the drug to a metabolically active form. Further, individuals lacking a biotransformation enzyme are often susceptible to cancers from environmental chemicals due to inability to detoxify the chemicals.

Human cytochrome P450 1A2 constitutes about 13% of total P450 in human liver and is the second most abundant P450 following human cytochrome P450 3A4. P450 1A2 catalyzes the metabolism of a large variety of drugs and carcinogens. Drugs metabolized by human P450 1A2 include phenacetin, R-warfarin, clomipramine, imipramine, theophyline, theobromine, paraxanthine, caffeine, chlorzoxazone, 7-methoxyresorufin, and 7-ethoxycoumarin. P450 1A2 also has a major role in activating mutagens and carcinogens. For example, 1A2 metabolically activates the food pyrolysis products IQ and MeIQx to active mutagens.

A complication in patient drug choice is that most drugs have not been characterized for their metabolism by P450 1A2 and other cytochromes P450. Without knowing which cytochrome(s) p450 is/are responsible for metabolizing an individual drug, an assessment cannot be made for the adequacy of a patient's P450 profile. For such drugs, there is a risk of adverse effects if the drugs are administered to deficient metabolizers.

The cytochrome P-450 3A (CYP 3A) isoenzyme is a member of the cytochrome P-450 superfamily. It constitutes up to 60% of the total human liver microsomal cytochrome P-450 and is responsible for metabolism of a large number of drugs including nifedipine, macrofide antibiotics including erythromycin and troleandomycin, cyclosporin, FK506, teffenadine, tamoxifen, lidocaine, midazolam, triazolam, dapsone, diltiazem, lovastatin, quinidine, ethylestradiol, testosterone, and alfentanil. In addition, CYP 3A has been shown to be involved in both bioactivation and detoxication pathways for several carcinogens in vitro.

The active form of CYP 3A has been found in other organs besides the liver including kidney epithelial cells, jejunal mucosa, and the lungs. In these organs, the amount of the cytochrome P450 protein is much lower then in the liver. In a study of human lung microsomes, presence and activity of CYP 3A has been demonstrated.

Presence of the cytochrome P-450 3A in the lung microsomes indicates that the drugs and other substances which are subject to CYP 3A (P450-3A) mediated metabolism may be partially metabolized in the lungs. This has been demonstrated for the topical steroid, beclomethasome dipropionate. It has also been shown that only about 10% of the drug released by an inhaler is available to the lungs. The remaining mount is retained in the spacer device and oral cavity. Steroids absorbed from the lungs and gastrointestinal tract are subsequently metabolized by hepatic cytochrome P450. Many drugs, such as prednisone, cyclosporin, cyclophosphamide, digitoxin, diazepam, ethinylestradiol, midazolam, triazolo-benzodiazepines, dihydropyridine calcium channel blockers, certain HMG-CoA reductase inhibitors, etc. are metabolized by a member of the CYP3A family, CYP3A4.

Human CYP2A6 is an important member of the CYP superfamily and is present in liver up to 1% of the total CYP content (Yun et al., 1991). Human CYP2A6 metabolically activates the carcinogens aflatoxin B1 (Yun et al., 1991), a tobacco-specific nitrosamine 4-methylnitrosamino)-1-(3-pyridyl)-1-butone (Crespi et al., 1991), and N-nitrosodiethylamine (Fernandez-Salguero & Gonzalez, 1995). CYP2A6 also carries out coumarin metabolism by aromatic hydroxylation in humans (Pearce et al., 1992). Coumarin 7-hydroxylation has been used as a marker for CYP2A6 activity in vitro (Yamano et al., 1990) and the basis for measuring the in vivo expression of CYP2A6 (Cholerton et al., 1992; Rautio et al., 1992). A genetic polymorphism has been found in CYP2A6 (Fernandez-Salguero et al., 1995) that is due to three variant allelic forms, i.e., CYP2A6*1, 2A6*2, 2A6*3, respectively (Daly et al., 1996).

Cytochrome P450 2D6, also known as debrisoquine hydroxylase, is the best characterized polymorphic P450 in the human population (Gonzalez et al., Nature 331:442–446 (1988)). A poor metabolizer phenotype has been reported which behaves as an autosomat recessive trait with an incidence between 5 and 10% in the white population of North America and Europe. Poor metabolizers exhibit negligible amounts of cytochrome P450 2D6 (Gonzales et al., supra). Genetic differences in cytochrome P450 2D6 may be associated with increased risk of developing environmental and occupational based diseases. See Gonzalez & Gelboin, J. Toxicology and Environmental Health 40, 289–308 (1993)).

There is some evidence that S-mephenytoin 4' hydroxylase activity resides in the cytochrome P450 2C family of enzymes. A number of 2C human variants (designated 2C8, 2C9 and 2C10) have been partially purified, and/or cloned. A comparison of the P450 2C cDNAs and their predicted amino acid sequences shows that about 70% of the amino acids are absolutely conserved among the human P450 2C subfamily. Some regions of human P450 2C protein sequences have particularly highly conservation, and these regions may participate in common P450 functions. Other regions show greater sequence divergence regions and are likely responsible for different substrate specificities between 2C members.

Several drugs for treating cardiovascular and psychiatric disorders are known substrates of cytochrome P450 2D6. (Dahl and Bertilsson, Pharmacogenetics 3, 61–70 (1993)), a situation that creates problems in prescribing such drugs. Although such drugs may be the most effective treatment for most of the population, physicians are reluctant to prescribe them due to the risk of adverse effects in poor metabolizers. Buchert et al., Pharmacogenetics 2, 2–11 (1992); Dahl et al., Pharmacogenetics 3, 61–70 (1993).

A complication in patient drug choice is that most drugs have not been characterized for their metabolism cytochromes P450. Without knowing which cytochrome(s) p450 is/are responsible for metabolizing an individual drug, an assessment cannot be made for the adequacy of a patient's P450 profile. For such drugs, there is a risk of adverse effects if the drugs are administered to deficient metabolizers.

The use of in vitro metabolism of therapeutic agents to address the potential in vivo induction, inhibition, drug-drug interaction and individual variability issues is known (for a recent review, see Rodrigues, 1994, Biochem. Pharmacol. 48: 2147–2156). Central to these studies is the unambiguous identification of specific drug-metabolizing enzyme(s), particularly human cytochrome P450 isoform(s) responsible for the metabolism of drugs. This objective can be achieved by using selective cytochrome P450 inhibitors, antibodies, recombinant cytochrome P450s and correlation analysis (Rodrigues, 1994, Biochem. Pharmacol. 48: 2147–2156).

Tripterygium Wilfordii Hook. F. (TW) is a native plant in China. Roots of plant Tripterygium Wilfordii Hook. F. contains bioactive components, primarily alkaloids, diterpenes and triterpenes. Historically, TW plant has been widely used in China to treat a variety of human diseases including autoimmune and/or inflammatory diseases for centuries. Studies have shown that diterpenes are major effective components in treating rheumatoid arthritis, chronic nephritis and some other diseases. However, there has been no study whatsoever on activities of each isolated diterpene compound nor any combinations thereof in human.

While the Tripterygium Wilfordii Hook. F. extract prepared according to the traditional method(s) has been used for treating autoimmune or inflammatory diseases for many years, each diterpene content in the preparations resulting from such method(s) varies from preparation to preparation and it has never been fully analyzed and quantified. Any attempt to quantify the major bioactive components has not been satisfactory so far due to the complexity of the extract composition and technical difficulties, where multiple compounds create great interference between the components among themselves. Hence, neither physicians nor patients have had informative knowledge about the amount of active components administered to the patients, although the medicine has been used for many years. As a result of such inconsistency in the drug dosages it is difficult for physicians to monitor the treatments following prognosis of the diseases. The lack of a well defined dosage regimens also prevents this herbal medicine, that has been proven highly effective in treating autoimmune and inflammatory diseases, from being further studied for the benefits of the public at large.

Despite that various TW extracts containing diterpenes have been reported to be effective for the treatment of autoimmune and/or inflammatory diseases, but such TW extracts may be highly toxic. There has been death report resulting from administration of certain TW extract. Ttriptolide (T10) has been reported as being carcinogenic or a major component causing significant side effects, while triptriolide (T11), tripdiolide (T8) and tripchlorolide (T4) are demonstrated to be the components having the most favorable therapeutic indexes, i.e. high efficacy and low toxicity in TW extract.

Studies on inhibition of cytochrome P450 enzyme activities is clearly of therapeutic importance. The co-administration of the TW extracts with another drug may increase or decrease the plasma level of the other drug, therefore, directly affect the efficacy of the other drug. In some instances, inhibition of the metabolism of other drugs by the TW extracts may result in or reduce the production of certain carcinogenic substances in the body. Accordingly, it is important for both drug development and clinical use to determine which cytochrome P450 enzymes are interact with the TW extracts, since cytochrome P450 enzymes are directly related to the metabolisms of many drugs.

Insofar as applicants know, there has been no study relating to drug interactions between any forms of the TW extracts and any other drugs. Without the knowledge of the profile of the TW extract drug interactions, it would be unlikely that the TW extracts will be of any significance in clinical or therapeutic uses.

The present invention provides a profile of the drug interactions of the TW extracts by investigating the effects of a particular form of the extracts, AHT-323A botanical extract, on a series of cytochrome P450 enzymes.

SUMMARY OF THE INVENTION

It is an object of this invention to provide a method of inhibiting cytochrome P450 enzymes selected from the group consisting of CYP1A2, CYP2A6 and CYP3A4 by administering an effective inhibition amount of AHT-323A botanical extract to a patient.

According to the present invention, the in vitro $IC_{50}$ values of the AHT-323A botanical extract for cytochrome P450 enzyme CYP1A2, CYP2A6 and CYP3A4 are about 0.176, 0.741 and 0.0366 mg/ml, respectively.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
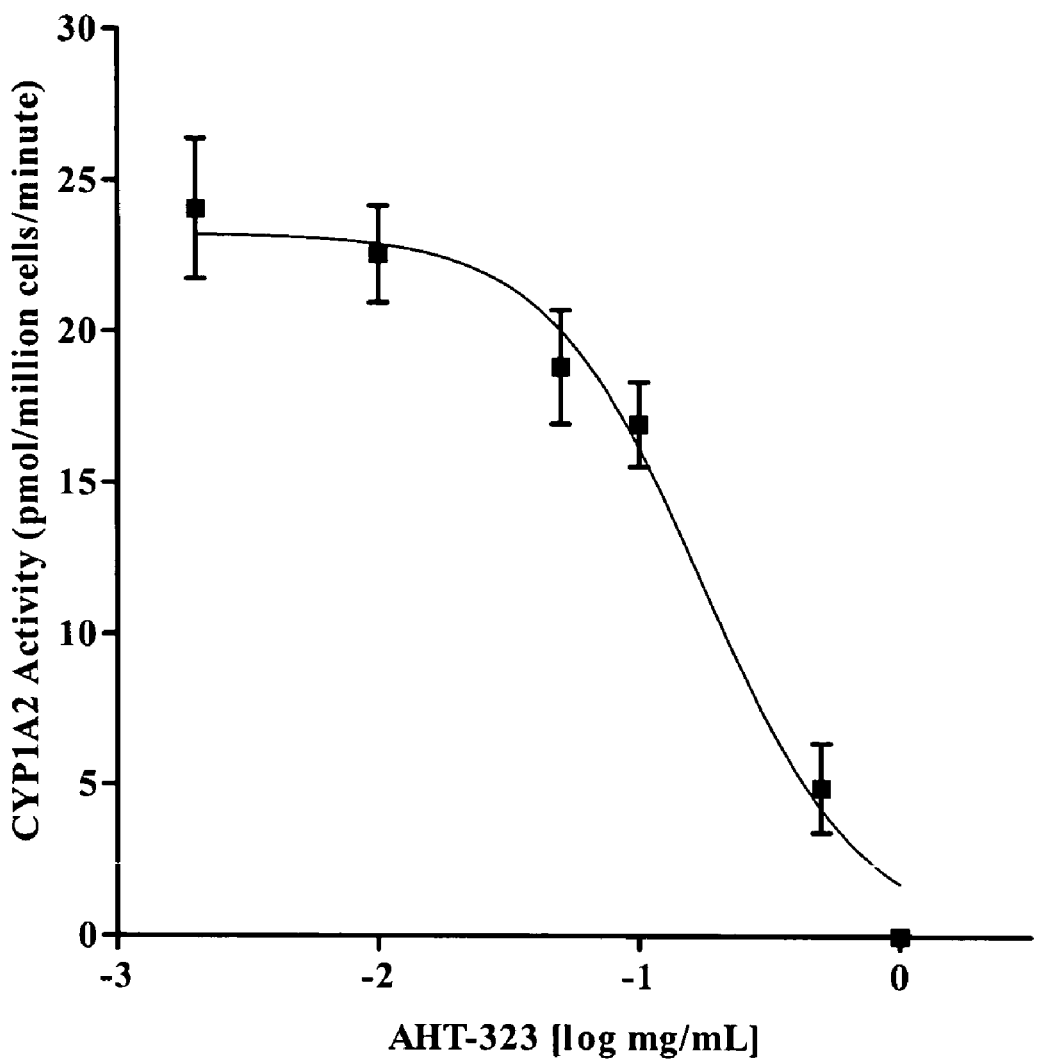
FIG. 1 depicts the inhibitory potential of AHT-323A botanical extract on CYP1A2 activity in cryopreserved human hepatocytes.

As used hereinabove and hereinafter, the term AHT-323A refers to a particular form of the TW extracts. The method of preparation, the composition and the properties of the AHT-323A botanical extract botanic extract are fully described in U.S. patent application Ser. No. 10/174,679, publication Number 20040018260, the content of which is hereby incorporated by reference in its entirety.

For example, AHT-323A botanical extract may generally prepared according to the following method, which is designed to maximize the therapeutic contents of T11, T4 and T8 in the extract, but to minimize the toxic content of T10.

The dried roots of Tripterygium Wilfordii Hook. F. ("TW"), are collected in P.R. China, examined and separated from other parts of the same plant or any foreign plants or contaminants prior to extraction. The roots of TW are then cut into small pieces, approximately 2×3 cm each, by any suitable tools such as a knife or a machine.

After cutting, the small pieces of the TW roots are loaded into an extractor that is commonly used in the industry and extracted with an industrial-grade alcohol, preferably, ethanol, for 3–5 times.

The supernatants from the alcohol extractions are combined and transferred to a recovery tank, which is commonly used in the industry. The alcohol is then recovered at room temperature under reduced pressure and an alcohol liquid extract of TW roots is thus obtained.

The alcohol extract so obtained is transferred to a large-scale chemical extractor commonly used in the industry, added with an adequate amount of industrial-grade chloroform at a volumetric ration of 3–6:1 (chloroform to extract), dissolved completely, and then filtered. The filtrate is collected in a storage tank. The remaining material was re-extracted with chloroform and filtered. The filtrate was added to the storage tank. This process was repeated (not more than four times) until the filtered extract appeared colorless under visual examination. The chloroform was then recovered and a dried crude powder extract was obtained by drying under heat and reduced pressure.

The crude powder from the chloroform extraction was then loaded (at a ratio of the crude extract to silica gel equaling to 1:10) onto a large-scale production silica gel columns (6 m×22 cm stainless steel silica gel column) that have been equilibrated with chloroform. The column was then eluted stepwise with chloroform solutions containing a gradient of ethanol ranging from 0.5–30%, respectively. The elution fractions were collected into cylindrical stainless steel containers.

Approximately 10,000 ml of chloroform-ethanol solution was used during the elution process for each column. The elution flow rate was about 20–25 drops per minutes. The first 5000 ml of elution solution was discarded followed by immediate collection of about 2000 ml of elution solution into 20 cylindrical stainless steel containers labeled as 1,2,3, . . . and 20, with about 100 ml each. The additional elution solution of about 3000 ml that followed was discarded as well.

The 2000 ml of the 20 elution fractions so collected in cylindrical stainless steel containers were tested for its chemical constituents of diterpenoid compounds by TLC. The fractions, showing positive for T4, T8 and T11 components, approximately from the containers or the fractions 6 to 14 (about 900 ml), were combined and concentrated via recovery of chloroform solvent at room temperature under a reduced pressure. The chloroform fluid extract was then obtained. To remove chloroform residue, the fractions were dissolved in ethanol, mixed and dried under heat and reduced pressure. This process may be repeated.

The dried extract, namely, AHT-323A botanical extract so produced may be ground to fine powder for further analysis.

The above described process yields about 0.15–0.30% AHT-323A botanical extract by weight, i.e., about 1.5–3 kilograms of AHT-323A botanical extract powder may be obtained from about 1000 kilograms of dried TW roots.

FIG. 1 of U.S. patent application Ser. No. 10/174,679 is a flow chart, which schematically shows a preferred process of the preparation of AHT-323A botanic extract.

In addition to the above exemplified method, any other techniques apparent to a person of ordinary skill in the art can be used to prepare an AHT-323A botanic extract having the substantially the same components and the same amounts of T11, T4, T8 and T10 as exemplarily described in U.S. patent application Ser. No. 10/174,679.

The terms CYP1A2, CYP2A6, CYP2C9, etc. represent isoforms of cytochrome P450 enzymes 1A2, 2A6, 2C9, etc. respectively.

Cryopreserved human hepatocytes represent a well-established system and commonly known to a person of ordinary skilled in the art, for the evaluation of the CYP450 inhibitory potential of xenobiotics (see reference 1 below). The purpose of this study was to determine the potential for AHT-323A botanical extract to inhibit cytochrome P450 (CYP450) isoforms 1A2, 2A6, 2C9, 2C19, 2D6, 2E1, and 3A4 in cryopreserved human hepatocytes.

CYP1A2 Activity

CYP1A2 activity was characterized by the formation of acetaminophen from phenacetin. No chromatographic interference from AHT-323A botanical extract was detected in the assay method (Table 1A). The activity of CYP1A2 was 91.6, 85.9, 71.5, 64.3, 18.6, and 0.00% of vehicle control (VC) in cryopreserved human hepatocytes treated with AHT-323A botanical extract at the tested concentrations of 0.002, 0.01, 0.05, 0.1, 0.5, and 1.0 mg/mL, respectively (Table 1B). The $IC_{50}$ value was estimated to be 0.176 mg/mL (FIG. 1).

TABLE 1A

CYP1A2 activity in cryopreserved human hepatocytes after administration of control articles

| Control Article | Conc. (mg/mL) | (μM) | Acetaminophen Formation (pmol/million cells/minute) | % VC | % Inhibition |
|---|---|---|---|---|---|
| VC | NA | 1.29 | 28.2 | | |
| | | 1.24 | 27.1 | | |
| | | 1.14 | 24.9 | | |
| | | 1.12 | 24.5 | | |
| | | 1.15 | 25.2 | | |
| | | 1.28 | 27.9 | | |
| | Mean ± SD | | 26.3 ± 1.6 | 100 | 0.00 |
| Furafylline | 1 μM | 0.363 | 7.93 | | |
| | | 0.334 | 7.30 | | |
| | | 0.323 | 7.07 | | |
| | | 0.336 | 7.33 | | |
| | | 0.333 | 7.27 | | |
| | | 0.323 | 7.07 | | |
| | Mean ± SD | | 7.33 ± 0.32 | 27.9 | 72.1 |
| CIC | 1 | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | Mean ± SD | | 0.00 | 0.00 | NA |

Abbreviations:
VC, vehicle control (2.0% acetonitrile);
CIC, chromatographic interference control;
SD, standard deviation;
NA, not applicable.

TABLE 1B

CYP1A2 activity in cryopreserved human hepatocytes after administration of VC and AHT-323A botanical extract

| Test/ Control Article | Conc. (mg/mL) | (μM) | Acetaminophen Formation (pmol/million cells/minute) | % VC | % Inhibition |
|---|---|---|---|---|---|
| VC | NA | 1.29 | 28.2 | | |
| | | 1.24 | 27.1 | | |
| | | 1.14 | 24.9 | | |
| | | 1.12 | 24.5 | | |
| | | 1.15 | 25.2 | | |
| | | 1.28 | 27.9 | | |
| | Mean ± SD | | 26.3 ± 1.6 | 100 | 0.00 |
| AHT-323A botanical extract | 0.002 | 1.22 | 26.7 | | |
| | | 1.06 | 23.2 | | |
| | | 1.02 | 22.3 | | |
| | Mean ± SD | | 24.1 ± 2.3 | 91.6 | 8.37 |
| | 0.01 | 0.978 | 21.4 | | |
| | | 1.01 | 21.9 | | |
| | | 1.12 | 24.4 | | |
| | Mean ± SD | | 22.6 ± 1.6 | 85.9 | 14.1 |
| | 0.05 | 0.959 | 20.9 | | |
| | | 0.843 | 18.4 | | |
| | | 0.787 | 17.2 | | |
| | Mean ± SD | | 18.8 ± 1.9 | 71.5 | 28.5 |
| | 0.1 | 0.723 | 15.8 | | |
| | | 0.754 | 16.5 | | |
| | | 0.847 | 18.5 | | |
| | Mean ± SD | | 16.9 ± 1.4 | 64.3 | 35.7 |
| | 0.5 | 0.302 | 6.60 | | |
| | | 0.191 | 4.17 | | |
| | | 0.180 | 3.93 | | |
| | Mean ± SD | | 4.90 ± 1.48 | 18.6 | 81.4 |
| | 1 | 0.00 | 0.00 | | |
| | | 0.00 | 0.00 | | |
| | | 0.00 | 0.00 | | |
| | Mean ± SD | | 0.00 | 0.00 | 100 |

Abbreviations:
VC, vehicle (2.0% acetonitrile);
SD, standard deviation;
NA, not applicable.

CYP2A6 Activity

Figure 2:
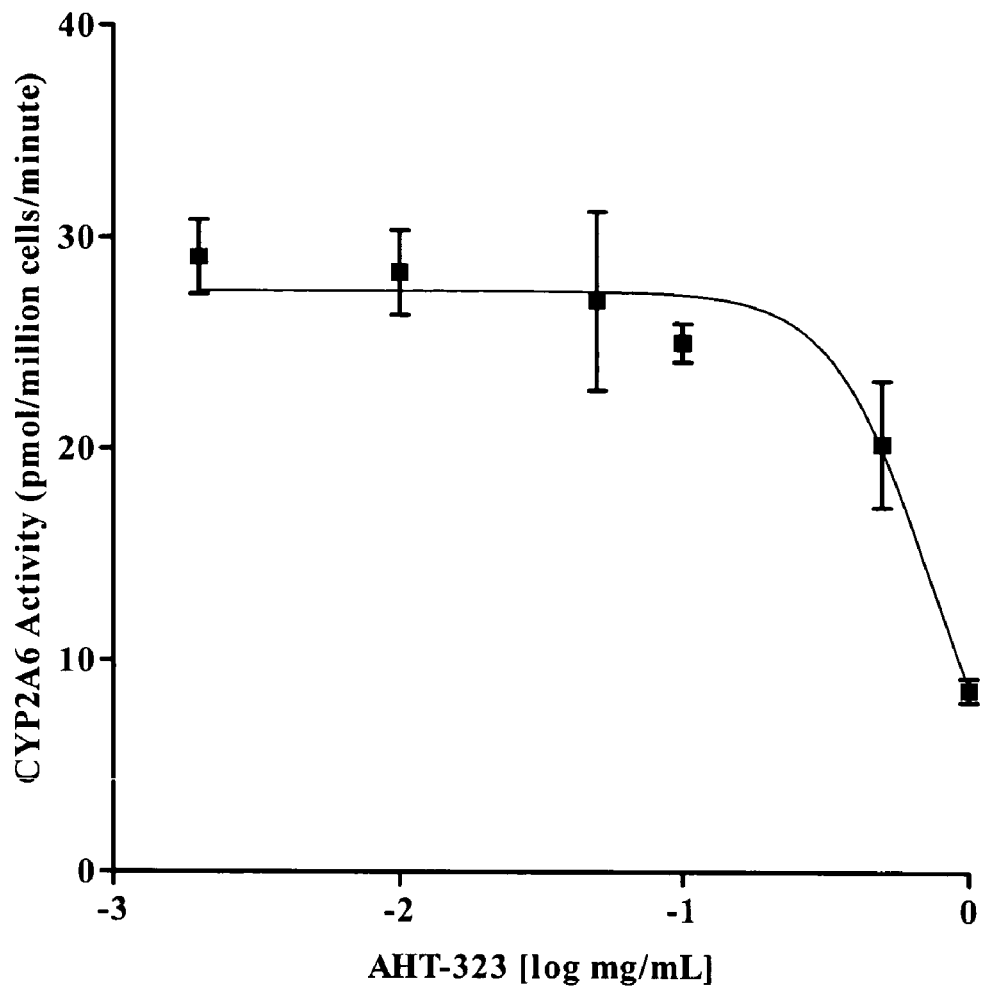
FIG. 2 depicts the inhibitory potential of AHT-323A botanical extract on CYP2A6 activity in cryopreserved human hepatocytes.

CYP2A6 activity was characterized by the formation of 7-hydroxycoumarin, 7-hydroxycoumarin glucuronide, and 7-hydroxycoumarin sulfate from coumarin. No chromatographic interference from AHT-323A botanical extract was detected in the assay method (Table 2A). The activity of CYP2A6 was 104, 101, 96.1, 89.0, 71.9, and 30.7% of VC in cryopreserved human hepatocytes treated with AHT-323A botanical extract at the tested concentrations of 0.002, 0.01, 0.05, 0.1, 0.5, and 1.0 mg/mL, respectively (Table 2B). The $IC_{50}$ value was estimated to be 0.741 mg/mL (FIG. 2).

TABLE 2A

CYP2A6 activity in cryopreserved human hepatocytes after administration of control articles

| Control Article | Conc. (mg/mL) | (μM) | Total Metabolite Formation (pmol/million cells/minute) | % VC | % Inhibition |
|---|---|---|---|---|---|
| VC | NA | 0.866 | 29.2 | | |
| | | 0.822 | 27.7 | | |
| | | 0.781 | 26.3 | | |
| | | 0.790 | 26.6 | | |
| | | 0.845 | 28.4 | | |
| | | 0.902 | 30.4 | | |
| | Mean ± SD | | 28.1 ± 1.6 | 100 | 0.00 |
| Tranylcy-promine | 3 μM | 0.331 | 11.1 | | |
| | | 0.291 | 9.80 | | |

TABLE 2A-continued

CYP2A6 activity in cryopreserved human hepatocytes after administration of control articles

| Control Article | Conc. (mg/mL) | (μM) | Total Metabolite Formation (pmol/million cells/minute) | % VC | % Inhibition |
|---|---|---|---|---|---|
| | | 0.283 | 9.53 | | |
| | | 0.340 | 11.4 | | |
| | | 0.235 | 7.90 | | |
| | | 0.317 | 10.7 | | |
| | Mean ± SD | | 10.1 ± 1.3 | 35.9 | 64.1 |
| CIC | 1 | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | Mean ± SD | | 0.00 | 0.00 | NA |

Abbreviations:
VC, vehicle control (2.0% acetonitrile);
CIC, chromatographic interference control;
SD, standard deviation;
NA, not applicable.

TABLE 2B

CYP2A6 activity in cryopreserved human hepatocytes after administration of VC and AHT-323A botanical extract

| Test Article | Conc. (mg/mL) | (μM) | Total Metabolite Formation (pmol/million cells/minute) | % VC | % Inhibition |
|---|---|---|---|---|---|
| VC | NA | 0.866 | 29.2 | | |
| | | 0.822 | 27.7 | | |
| | | 0.781 | 26.3 | | |
| | | 0.790 | 26.6 | | |
| | | 0.845 | 28.4 | | |
| | | 0.902 | 30.4 | | |
| | Mean ± SD | | 28.1 ± 1.6 | 100 | 0.00 |
| AHT-323A botanical extract | 0.002 | 0.923 | 31.1 | | |
| | | 0.840 | 28.3 | | |
| | | 0.827 | 27.8 | | |
| | Mean ± SD | | 29.1 ± 1.8 | 104 | −3.56 |
| | 0.01 | 0.773 | 26.0 | | |
| | | 0.879 | 29.6 | | |
| | | 0.874 | 29.4 | | |
| | Mean ± SD | | 28.3 ± 2.0 | 101 | −0.712 |
| | 0.05 | 0.947 | 31.9 | | |
| | | 0.732 | 24.6 | | |
| | | 0.727 | 24.5 | | |
| | Mean ± SD | | 27.0 ± 4.2 | 96.1 | 3.91 |
| | 0.1 | 0.738 | 24.8 | | |
| | | 0.719 | 24.2 | | |
| | | 0.771 | 26.0 | | |
| | Mean ± SD | | 25.0 ± 0.9 | 89.0 | 11.0 |
| | 0.5 | 0.701 | 23.6 | | |
| | | 0.566 | 19.1 | | |
| | | 0.536 | 18.0 | | |
| | Mean ± SD | | 20.2 ± 3.0 | 71.9 | 28.1 |
| | 1 | 0.271 | 9.13 | | |
| | | 0.238 | 8.00 | | |
| | | 0.259 | 8.73 | | |
| | Mean ± SD | | 8.62 ± 0.57 | 30.7 | 69.3 |

Abbreviations:
VC, vehicle control (2.0% acetonitrile);
SD, standard deviation;
NA, not applicable.

CYP2C9 Activity

CYP2C9 activity was characterized by the formation of 4-hydroxytolbutamide from tolbutamide. In the initial study, no data were available to evaluate the effects of AHT-323A botanical extract on CYP2C9 activity in cryopreserved human hepatocytes due to the impurity of tolbutamide. Therefore, reincubations were conducted to evaluate the effects of AHT-323A botanical extract on this isoform.

In the subsequent reincubation, no conclusion could be drawn on the effects of AHT-323A botanical extract at all dose levels due to chromatographic interference (Tables 3A and 3B).

TABLE 3A

CYP2C9 activity in cryopreserved human hepatocytes after administration of control articles

| Control Article | Conc. (mg/mL) | (μM) | 4-Hydroxytolbutamide Formation (pmol/million cells/minute) | % VC | % Inhibition |
|---|---|---|---|---|---|
| VC | NA | 1.32 | 44.7 | | |
| | | 1.27 | 42.7 | | |
| | | 1.27 | 43.0 | | |
| | | 1.28 | 43.0 | | |
| | | 1.27 | 42.7 | | |
| | | 1.35 | 45.7 | | |
| | Mean ± SD | | 43.6 ± 1.3 | 100 | 0.00 |
| Sulfaphenazole | 10 μM | 0.074 | 2.49 | | |
| | | 0.064 | 2.15 | | |
| | | 0.056 | 1.89 | | |
| | | 0.064 | 2.15 | | |
| | | 0.070 | 2.36 | | |
| | | 0.062 | 2.09 | | |
| | Mean ± SD | | 2.19 ± 0.21 | 5.02 | 95.0 |
| CIC | 1 | NQ | NQ | | |
| | | NQ | NQ | | |
| | | NQ | NQ | | |
| | | NQ | NQ | | |
| | | NQ | NQ | | |
| | | NQ | NQ | | |
| | Mean ± SD | | NQ | NA | NA |

Abbreviations:
VC, vehicle control (2.0% acetonitrile);
CIC, chromatographic interference control;
SD, standard deviation;
NA, not applicable;
NQ, not quantifiable.

TABLE 3B

CYP2C9 activity in cryopreserved human hepatocytes after administration of VC and AHT-323A botanical extract

| Test Article | Conc. (mg/mL) | (μM) | 4-Hydroxytolbutamide Formation (pmol/million cells/minute) | % VC | % Inhibition |
|---|---|---|---|---|---|
| VC | NA | 1.32 | 44.7 | | |
| | | 1.27 | 42.7 | | |
| | | 1.27 | 43.0 | | |
| | | 1.28 | 43.0 | | |
| | | 1.27 | 42.7 | | |
| | | 1.35 | 45.7 | | |
| | Mean ± SD | | 43.6 ± 1.3 | 100 | 0.00 |
| AHT-323A botanical extract | 0.002 | 1.16 | 39.3 | | |
| | | 1.13 | 38.0 | | |
| | | 1.12 | 37.7 | | |
| | Mean ± SD | | 38.3 ± 0.9 | 87.8 | −12.1 |
| | 0.01 | 1.05 | 35.3 | | |
| | | 1.04 | 35.0 | | |
| | | 1.06 | 35.7 | | |
| | Mean ± SD | | 35.3 ± 0.4 | 81.0 | −21.0 |
| | 0.05 | 0.794 | 26.7 | | |
| | | 0.699 | 23.5 | | |
| | | 0.665 | 22.4 | | |
| | Mean ± SD | | 24.2 ± 2.2 | 55.5 | −40.3 |
| | 0.1 | NQ | NQ | | |

TABLE 3B-continued

CYP2C9 activity in cryopreserved human hepatocytes after administration of VC and AHT-323A botanical extract

| Test Article | Conc. (mg/mL) | (μM) | 4-Hydroxytolbutamide Formation (pmol/million cells/minute) | % VC | % Inhibition |
|---|---|---|---|---|---|
| | | NQ | NQ | | |
| | | NQ | NQ | | |
| | Mean ± SD | | NQ | NA | NA |
| | 0.5 | NQ | NQ | | |
| | | NQ | NQ | | |
| | | NQ | NQ | | |
| | Mean ± SD | | NQ | NA | NA |
| | 1 | NQ | NQ | | |
| | | NQ | NQ | | |
| | | NQ | NQ | | |
| | Mean ± SD | | NQ | NA | NA |

Abbreviations:
VC, vehicle control (2.0% acetonitrile);
SD, standard deviation;
NA, not applicable;
NQ, not quantifiable.

CYP2C19 Activity

CYP2C19 activity was characterized by the formation of 4'hydroxy-S-mephenytoin from S-mephenytoin. No conclusion could be drawn on the effects of AHT-323A botanical extract at all dose levels due to chromatographic interference (Tables 4A and 4B).

TABLE 4A

CYP2C19 activity in cryopreserved human hepatocytes after administration of control articles

| Control Article | Conc. (mg/mL) | (μM) | 4-Hydroxymephenytoin Formation (pmol/million cells/minute) | % VC | % Inhibition |
|---|---|---|---|---|---|
| VC | NA | 0.973 | 18.0 | | |
| | | 1.02 | 18.9 | | |
| | | 0.965 | 17.9 | | |
| | | 0.990 | 18.3 | | |
| | | 0.967 | 17.9 | | |
| | | 0.969 | 17.9 | | |
| | Mean ± SD | | 18.2 ± 0.4 | 100 | 0.00 |
| Omeprazole | 25 μM | 0.703 | 13.0 | | |
| | | 0.721 | 13.3 | | |
| | | 0.735 | 13.6 | | |
| | | 0.710 | 13.1 | | |
| | | 0.731 | 13.5 | | |
| | | 0.761 | 14.1 | | |
| | Mean ± SD | | 13.4 ± 0.4 | 73.6 | 26.4 |
| CIC | 1 | 6.14 | 114 | | |
| | | 6.17 | 114 | | |
| | | 6.09 | 113 | | |
| | | 6.02 | 111 | | |
| | | 6.02 | 111 | | |
| | | 6.11 | 113 | | |
| | Mean ± SD | | 113 ± 1 | 621 | NA |

Abbreviations:
VC, vehicle control (2.0% acetonitrile);
CIC, chromatographic interference control;
SD, standard deviation;
NA, not applicable.

TABLE 4B

CYP2C19 activity in cryopreserved human hepatocytes after administration of VC and AHT-323A botanical extract

| Test Article | Conc. (mg/mL) | (μM) | 4-Hydroxymephenytoin Formation (pmol/million cells/minute) | % VC | % Inhibition |
|---|---|---|---|---|---|
| VC | NA | 0.973 | 18.0 | | |
| | | 1.02 | 18.9 | | |
| | | 0.965 | 17.9 | | |
| | | 0.990 | 18.3 | | |
| | | 0.967 | 17.9 | | |
| | | 0.969 | 17.9 | | |
| | Mean ± SD | | 18.2 ± 0.4 | 100 | 0.00 |
| AHT-323A botanical extract | 0.002 | 1.03 | 19.0 | | |
| | | 1.05 | 19.5 | | |
| | | 1.03 | 19.0 | | |
| | Mean ± SD | | 19.2 ± 0.3 | 105 | -5.49 |
| | 0.01 | 1.06 | 19.6 | | |
| | | 1.08 | 19.9 | | |
| | | 1.04 | 19.2 | | |
| | Mean ± SD | | 19.6 ± 0.4 | 108 | -7.69 |
| | 0.05 | 1.20 | 22.2 | | |
| | | 1.20 | 22.3 | | |
| | | 1.22 | 22.6 | | |
| | Mean ± SD | | 22.4 ± 0.2 | 123 | -23.1 |
| | 0.1 | 1.54 | 28.4 | | |
| | | 1.53 | 28.3 | | |
| | | 1.43 | 26.4 | | |
| | Mean ± SD | | 27.7 ± 1.1 | 152 | -52.2 |
| | 0.5 | 3.59 | 66.3 | | |
| | | 3.55 | 65.7 | | |
| | | 3.44 | 63.7 | | |
| | Mean ± SD | | 65.2 ± 1.4 | 358 | -258 |
| | 1 | 5.75 | 106 | | |
| | | 6.13 | 113 | | |
| | | 6.19 | 115 | | |
| | Mean ± SD | | 111 ± 5 | 610 | -510 |

Abbreviations:
VC, vehicle control (2.0% acetonitrile);
SD, standard deviation;
NA, not applicable.

CYP2D6 Activity

CYP2D6 activity was characterized by the formation of dextrorphan from dextromethorphan. No conclusion could be drawn on the effects of AHT-323A botanical extract at all dose levels due to chromatographic interference (Tables 5A and 5B).

TABLE 5A

CYP2D6 activity in cryopreserved human hepatocytes after administration of control articles

| Test/ Control Article | Conc. (mg/mL) | (μM) | Dextrorphan Formation (pmol/million cells/minute) | % VC | % Inhibition |
|---|---|---|---|---|---|
| VC | NA | 0.239 | 8.03 | | |
| | | 0.227 | 7.63 | | |
| | | 0.230 | 7.73 | | |
| | | 0.213 | 7.17 | | |
| | | 0.228 | 7.67 | | |
| | | 0.251 | 8.47 | | |
| | Mean ± SD | | 7.78 ± 0.44 | 100 | 0.00 |
| Quinidine | 2.5 nM | 0.044* | 1.48 | | |
| | | 0.040* | 1.35 | | |
| | | 0.044* | 1.48 | | |
| | | 0.043* | 1.45 | | |
| | | 0.044* | 1.48 | | |
| | | 0.049* | 1.65 | | |
| | Mean ± SD | | 1.48 ± 0.10 | NA | NA |
| CIC | 1 | 0.628 | 21.1 | | |
| | | 0.656 | 22.1 | | |

TABLE 5A-continued

CYP2D6 activity in cryopreserved human hepatocytes after administration of control articles

| Test/Control Article | Conc. (mg/mL) | (μM) | Dextrorphan Formation (pmol/million cells/minute) | % VC | % Inhibition |
|---|---|---|---|---|---|
| | | 0.624 | 21.0 | | |
| | | 0.631 | 21.2 | | |
| | | 0.609 | 20.5 | | |
| | | 0.631 | 21.2 | | |
| | Mean ± SD | | 21.2 ± 0.5 | 272 | NA |

*Observed analyzed value was below quantifiable limit (0.0955 μM).
Abbreviations:
VC, vehicle control (2.0% acetonitrile);
CIC, chromatographic interference control;
SD, standard deviation;
NA, not applicable.

TABLE 5B

CYP2D6 activity in cryopreserved human hepatocytes after administration of VC and AHT-323A botanical extract

| Test/Control Article | Conc. (mg/mL) | (μM) | Dextrorphan Formation (pmol/million cells/minute) | % VC | % Inhibition |
|---|---|---|---|---|---|
| VC | NA | 0.239 | 8.03 | | |
| | | 0.227 | 7.63 | | |
| | | 0.230 | 7.73 | | |
| | | 0.213 | 7.17 | | |
| | | 0.228 | 7.67 | | |
| | | 0.251 | 8.47 | | |
| | Mean ± SD | | 7.78 ± 0.44 | 100 | 0.00 |
| AHT-323A botanical extract | 0.002 | 0.231 | 7.77 | | |
| | | 0.235 | 7.90 | | |
| | | 0.197 | 6.63 | | |
| | Mean ± SD | | 7.43 ± 0.70 | 95.5 | 4.50 |
| | 0.01 | 0.223 | 7.50 | | |
| | | 0.233 | 7.83 | | |
| | | 0.240 | 8.07 | | |
| | Mean ± SD | | 7.80 ± 0.29 | 100 | −0.26 |
| | 0.05 | 0.210 | 7.07 | | |
| | | 0.211 | 7.10 | | |
| | | 0.184 | 6.20 | | |
| | Mean ± SD | | 6.79 ± 0.51 | 87.3 | 12.7 |
| | 0.1 | 0.200 | 6.73 | | |
| | | 0.231 | 7.77 | | |
| | | 0.226 | 7.60 | | |
| | Mean ± SD | | 7.37 ± 0.56 | 94.7 | 5.27 |
| | 0.5 | 0.400 | 13.5 | | |
| | | 0.386 | 13.0 | | |
| | | 0.388 | 13.1 | | |
| | Mean ± SD | | 13.2 ± 0.3 | 170 | −69.7 |
| | 1 | 0.681 | 22.9 | | |
| | | 0.675 | 22.7 | | |
| | | 0.694 | 23.4 | | |
| | Mean ± SD | | 23.0 ± 0.4 | 296 | −196 |

Abbreviations:
VC, vehicle control (2.0% acetonitrile);
CIC, chromatographic interference control;
SD, standard deviation;
NA, not applicable.

CYP2E1 Activity

CYP2E1 activity was characterized by the formation of 6-hydroxychlorzoxazone from chlorzoxazone. No chromatographic interference from AHT-323A botanical extract was detected in the assay method (Table 6A). The activity of CYP2E1 was 105, 109, 113, 119, 143, and 119% of VC in cryopreserved human hepatocytes treated with AHT-323A botanical extract at the tested concentrations of 0.002, 0.01, 0.05, 0.1, 0.5. and 1.0 mg/mL, respectively (Table 6B). Since there was no inhibition of CYP2E1 activity at all dose levels, the $IC_{50}$ value was not calculated.

TABLE 6A

CYP2E1 activity in cryopreserved human hepatocytes after administration of control articles

| Test/Control Article | Conc. (mg/mL) | (μM) | 6-Hydroxychlorzoxazone Formation (pmol/million cells/minute) | % VC | % Inhibition |
|---|---|---|---|---|---|
| VC | NA | 0.620 | 20.9 | | |
| | | 0.617 | 20.8 | | |
| | | 0.564 | 19.0 | | |
| | | 0.572 | 19.3 | | |
| | | 0.578 | 19.5 | | |
| | | 0.587 | 19.8 | | |
| | Mean ± SD | | 19.9 ± 0.8 | 100 | 0 |
| 4-Methyl-pyrazole | 250 μM | 0.138 | 4.63 | | |
| | | 0.140 | 4.70 | | |
| | | 0.117 | 3.93 | | |
| | | 0.136 | 4.57 | | |
| | | 0.141 | 4.73 | | |
| | | 0.152 | 5.13 | | |
| | Mean ± SD | | 4.62 ± 0.39 | 23.2 | 76.8 |
| CIC | 1 | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | Mean ± SD | | 0.00 | 0.00 | NA |

Abbreviations: VC, vehicle control (2.0% acetonitrile);
CIC, chromatographic interference control;
SD, standard deviation;
NA, not applicable.

TABLE 6B

CYP2E1 activity in cryopreserved human hepatocytes after administration of VC and AHT-323A botanical extract

| Test/Control Article | Conc. (mg/mL) | (μM) | 6-Hydroxychlorzoxazone Formation (pmol/million cells/minute) | % VC | % Inhibition |
|---|---|---|---|---|---|
| VC | NA | 0.620 | 20.9 | | |
| | | 0.617 | 20.8 | | |
| | | 0.564 | 19.0 | | |
| | | 0.572 | 19.3 | | |
| | | 0.578 | 19.5 | | |
| | | 0.587 | 19.8 | | |
| | Mean ± SD | | 19.9 ± 0.8 | 100 | 0 |
| AHT-323A botanical extract | 0.002 | 0.624 | 21.0 | | |
| | | 0.604 | 20.3 | | |
| | | 0.624 | 21.0 | | |
| | Mean ± SD | | 20.8 ± 0.4 | 105 | −4.52 |
| | 0.01 | 0.621 | 20.9 | | |
| | | 0.653 | 22.0 | | |
| | | 0.652 | 22.0 | | |
| | Mean ± SD | | 21.6 ± 0.6 | 109 | −8.54 |
| | 0.05 | 0.677 | 22.8 | | |
| | | 0.669 | 22.5 | | |
| | | 0.652 | 22.0 | | |
| | Mean ± SD | | 22.4 ± 0.4 | 113 | −12.6 |
| | 0.1 | 0.700 | 23.6 | | |
| | | 0.698 | 23.5 | | |
| | | 0.715 | 24.1 | | |
| | Mean ± SD | | 23.7 ± 0.3 | 119 | −19.1 |
| | 0.5 | 0.833 | 28.0 | | |
| | | 0.863 | 29.1 | | |
| | | 0.845 | 28.4 | | |

TABLE 6B-continued

CYP2E1 activity in cryopreserved human hepatocytes after
administration of VC and AHT-323A botanical extract

| Test/<br>Control<br>Article | Conc.<br>(mg/mL) | (μM) | 6-Hydroxychlorzoxazone Formation | | |
|---|---|---|---|---|---|
| | | | (pmol/million<br>cells/minute) | %<br>VC | %<br>Inhibition |
| | Mean ± SD | | 28.5 ± 0.6 | 143 | −43.2 |
| | 1 | 0.719 | 24.2 | | |
| | | 0.698 | 23.5 | | |
| | | 0.692 | 23.3 | | |
| | Mean ± SD | | 23.7 ± 0.5 | 119 | −19.1 |

Abbreviations: VC, vehicle control (2.0% acetonitrile);
SD, standard deviation;
NA, not applicable.

CYP3A4 Activity

Figure 3:
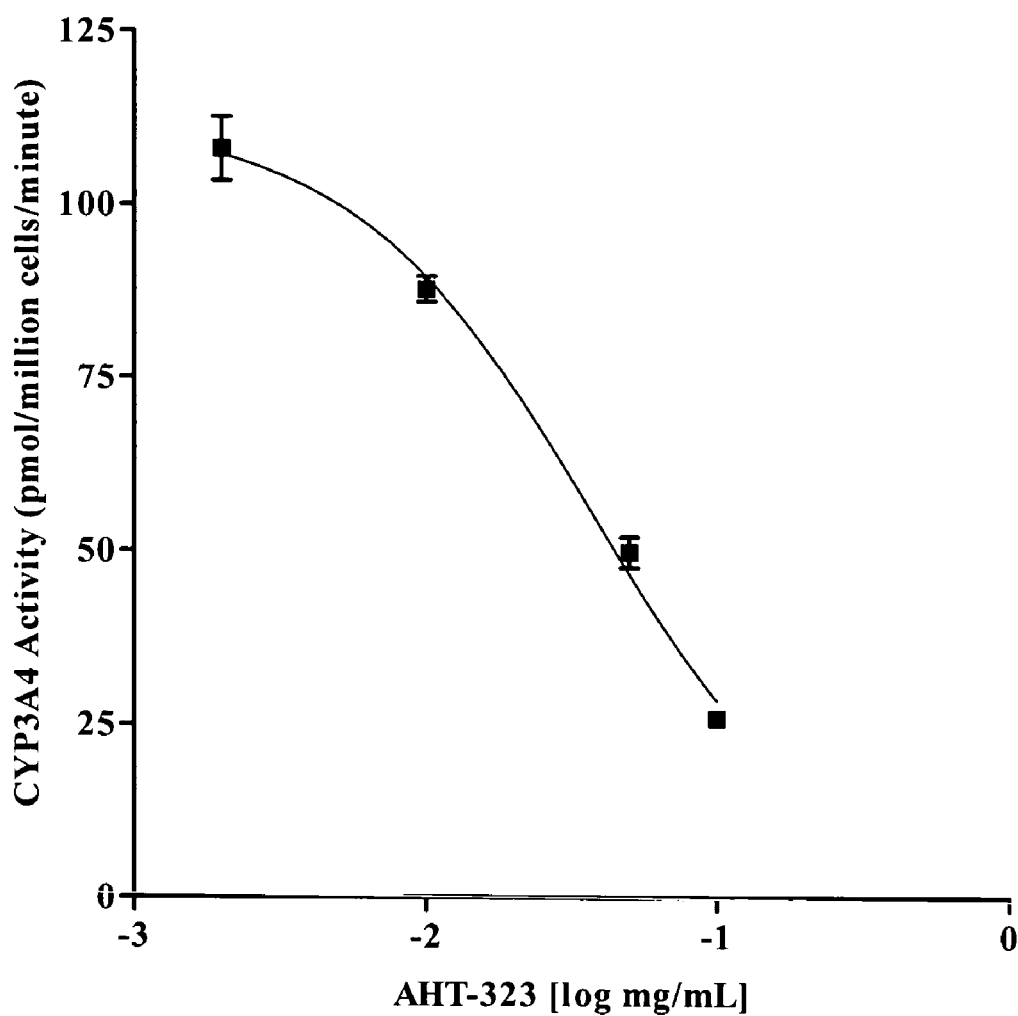
FIG. 3 depicts the inhibitory potential of AHT-323A botanical extract on CYP3A4 activity in cryopreserved human hepatocytes.

CYP3A4 activity was characterized by the formation of 6β-hydroxytestosterone from testosterone. No chromatographic interference from AHT-323A botanical extract was detected in the assay method (Table 7A). The activity of CYP3A4 was 86.4, 70.2, 39.8, and 20.6% of VC in cryopreserved human hepatocytes treated with AHT-323A botanical extract at the tested concentrations of 0.002, 0.01, 0.05, and 0.1 mg/mL, respectively (Table 7B). The percent of VC of CYP3A4 activity in cryopreserved human hepatocytes treated with AHT-323A botanical extract at the tested concentrations of 0.5 or 1.0 mg/mL could not be calculated since CYP3A4 activity was below the limit of quantitation (Table 7B). The $IC_{50}$ value was estimated to be 0.0366 mg/mL (FIG. 3).

TABLE 7A

CYP3A4 activity in cryopreserved human hepatocytes
after administration of control articles

| Test/<br>Control<br>Article | Conc.<br>(mg/mL) | (μM) | 6β-Hydroxytestosterone Formation | | |
|---|---|---|---|---|---|
| | | | (pmol/million<br>cells/minute) | %<br>VC | %<br>Inhibition |
| VC | NA | 3.95 | 133 | | |
| | | 3.71 | 125 | | |
| | | 3.66 | 123 | | |
| | | 3.61 | 121 | | |
| | | 3.61 | 122 | | |
| | | 3.73 | 125 | | |
| | Mean ± SD | | 125 ± 4 | 100 | 0.00 |
| Keto-<br>conazole | 1 μM | 0.281 | 9.47 | | |
| | | 0.249 | 8.37 | | |
| | | 0.254 | 8.57 | | |
| | | 0.238 | 8.00 | | |
| | | 0.248 | 8.33 | | |
| | | 0.271 | 9.13 | | |
| | Mean ± SD | | 8.65 ± 0.55 | 6.92 | 93.1 |
| CIC | 1 | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | | 0.00 | 0.00 | | |
| | Mean ± SD | | 0.00 | 0.00 | NA |

Abbreviations: VC, vehicle control (2.0% acetonitrile);
CIC, chromatographic interference control;
SD, standard deviation;
NA, not applicable.

TABLE 7B

CYP3A4 activity in cryopreserved human hepatocytes after
administration of VC and AHT-323A botanical extract

| Test/<br>Control<br>Article | Conc.<br>(mg/mL) | (μM) | 6β-Hydroxytestosterone Formation | | |
|---|---|---|---|---|---|
| | | | (pmol/million<br>cells/minute) | %<br>VC | %<br>Inhibition |
| VC | NA | 3.95 | 133 | | |
| | | 3.71 | 125 | | |
| | | 3.66 | 123 | | |
| | | 3.61 | 121 | | |
| | | 3.61 | 122 | | |
| | | 3.73 | 125 | | |
| | Mean ± SD | | 125 ± 4 | 100 | 0.00 |
| AHT-323A<br>botanical<br>extract | 0.002 | 3.35 | 113 | | |
| | | 3.19 | 107 | | |
| | | 3.09 | 104 | | |
| | Mean ± SD | | 108 ± 5 | 86.4 | 13.6 |
| | 0.01 | 2.56 | 86.0 | | |
| | | 2.60 | 87.7 | | |
| | | 2.67 | 89.7 | | |
| | Mean ± SD | | 87.8 ± 1.9 | 70.2 | 29.8 |
| | 0.05 | 1.56 | 52.3 | | |
| | | 1.44 | 48.7 | | |
| | | 1.44 | 48.3 | | |
| | Mean ± SD | | 49.8 ± 2.2 | 39.8 | 60.2 |
| | 0.1 | 0.763 | 25.7 | | |
| | | 0.766 | 25.8 | | |
| | | 0.771 | 26.0 | | |
| | Mean ± SD | | 25.8 ± 0.2 | 20.6 | 79.4 |
| | 0.5 | 0.159* | 5.37 | | |
| | | 0.156* | 5.27 | | |
| | | 0.145* | 4.87 | | |
| | Mean ± SD | | 5.17 ± 0.26 | NA | NA |
| | 1 | 0.085* | 2.86 | | |
| | | 0.081* | 2.73 | | |
| | | 0.078* | 2.63 | | |
| | Mean ± SD | | 2.74 ± 0.12 | NA | NA |

*Observed analyzed value was below quantifiable limit (0.2 μM).
Abbreviations: VC, vehicle control (2.0% acetonitrile);
SD, standard deviation;
NA, not applicable.

Data Evaluation

The formation of each metabolite from CYP450 isoform substrates were quantified using an analytical method specifically designed for this type of analysis. Data are reported as specific activity (pmol/million cells/minute) and as percentage of VC using the following equation:

$$\% \text{ of } VC = \frac{\text{Activity of treatment}}{\text{Activity of } VC} \times 100$$

Descriptive statistics (mean and standard deviation) of each test article concentration were calculated, using Microsoft® Excel 97, and are presented to show inhibitory potency. The $IC_{50}$ value for the test article on each CYP450 isoform was calculated using GraphPad Prism® Version 3.02 where possible.

In summary, no inhibition was observed for CYP2E1 activity in cryopreserved human hepatocytes treated with AHT-323A botanical extract at concentrations up to 1.0 mg/mL. The $IC_{50}$ values for CYP1A2, CYP2A6, and CYP3A4 activities were estimated to be 0.176, 0.741, and 0.0366 mg/mL, respectively. No conclusion could be drawn on the effect of AHT-323A botanical extract at all tested dose levels on the activities of CYP2C9, CYP2C19, and CYP2D6, due to chromatographic interference from incubations of AHT-323A botanical extract with cryopreserved human hepatocytes. AHT-323A botanical extract botanical may therefore potentially increase the plasma concentrations of the drugs that are metabolized by CYP1A2, CYP2A6, and/or CYP3A4. The examples of such drugs may include but are not limited to acetaminophen and caffeine, that are metabolized by CYP1A2; coumarin by CYP2A6; and the drugs metabolized by CYP3A4, such as prednisone, cyclosporin, cyclophosphamide, digitoxin, diazepam, ethinylestradiol, midazolam, triazolo-benzodiazepines, dihydropyridine calcium channel blockers, certain HMG-CoA reductase inhibitors, etc. Particular caution is recommended when administering AHT-323A botanical extract with CYP3A4 substrates that have a narrow therapeutic window, e.g. prednisone, cyclophosphamide cyclosporine or pimozide.

The following references are intended to further explain or illustrate the present invention. They are hereby incorporated by reference in their entirety.

REFERENCES

1. Li, A. P., Lu, C., Brent, J. A., Pham, C., Fackett, A., Ruegg, C. E., and Silber, P. M. (1999). Cryopreserved human hepatocytes: characterization of drug-metabolizing enzyme activities and applications in higher throughput screening assays for hepatotoxicity, metabolic stability, and drug-drug interaction potential. *Chem. Biol. Interact.* 121, 17–35.
2. Li, A. P., Roque, M. A., Beck, D. J., and Kaminski, D. L. (1992). Isolation and culturing of hepatocytes from human liver. *J. Tiss. Culture Methods* 14, 139–146.
3. Loretz, L. J., Li, A. P., Flye, M. W., and Wilson, A. G. (1989). Optimization of cryopreservation procedures for rat and human hepatocytes. *Xenobiotica* 19(5), 489–498.
4. Ruegg, C. E., Silber, P. M., Mughal, R. A., Ismail, J., Lu, C., Bode, D. C., and Li, A. P. (1997). Cytochrome-P450 induction and conjugated metabolism in primary human hepatocytes after cryopreservation. *In Vitro Toxicol.* 10(2), 217–222.

The following examples represent some particular embodiments of the present invention, which shall not be construed as limitations of various aspects of the present invention.

EXAMPLE 1

Incubation Conditions and Sample Size

All incubations were conducted at 37° C., 95% air/5% $CO_2$, and saturating humidity. The sample size was N=3 replicates for experimental groups and N=6 replicates for control groups.

EXAMPLE 2

Media

The following media as prepared at the study laboratory were used in this study.

Suspension medium: Dulbecco's modified Ragle's medium stock supplemented with additional bovine serum albumin, fetal bovine serum, and insulin.

Substrate medium: Krebs-Henseleit buffer supplemented with amikacin, calcium chloride, gentamicin, N-(2-hydroxyethyl) piperazine-N'-(2-ethanesulfonate), heptanoic acid, and sodium bicarbonate.

EXAMPLE 3

Test Article Information and Preparation

The test article was identified in this study is AHT-323A botanical extract, the preparation, composition and properties of which are described in U.S. patent application Ser. No. 10/174,679, which is hereby incorporated by reference.

The test article was prepared in acetonitrile as 100× stock solutions and diluted with substrate media to prepare 2× dosing solutions which, when added to the hepatocyte suspensions, achieved final dosing concentrations of 0.002, 0.01, 0.05, 0.1, 0.5, and 1 mg/mL, each containing 1% acetonitrile.

EXAMPLE 4

Hepatocyte Isolation and Incubation

The following demographics and medical history of the human donors of the hepatocyte are provided to the study laboratory:

Study lot no. 88 was an 84-year-old Caucasian female who died from a closed head injury. Urinalyses and blood chemistries were within normal limits. Serologies were negative except for cytomegalovirus. The donor had been taking estrogen. No chronic medications were listed.

Study lot no. 97 was a 47-year-old Caucasian male who died from an intracranial bleed. Urinalyses and blood chemistries were within normal limits. Serologies were negative except for cytomegalovirus. The donor had a history of gout, hypertension, Type 2 diabetes, seasonal asthma, and yellow jaundice. The donor used alcohol (1–2 beers on an infrequent daily basis, quit 10 years prior to death), tobacco products (1 pack/day for 20 years, quit 10 years prior to death). The donor took Allepurinol, Nortriptylene, and Norvase on a regular basis.

Study lot no. 109 was a 69-year-old Caucasian male who died from a subdural hematoma. Urinalyses and blood chemistries were within normal limits. Serologies were negative except for cytomegalovirus. The donor had high blood pressure, high cholesterol, non-insulin-dependent diabetes mellitus, and transitional cell cancer. The donor used alcohol (on weekends) and tobacco (2 to 3 packs per day for over 25 years; quit 6 years prior to death). No chronic medications were listed.

Study lot no. 117 was a 47-year old Caucasian female who died from asystole. Urinalyses and blood chemistries were within normal limits. Serologies were negative. Cytomegalovirus testing was not done. The donor had a history of tobacco use (less than half a pack daily, quit 3–4 years prior to death). No chronic medications were listed.

Study lot no. 120 was a 62-year-old Caucasian male who died of a gunshot wound to the head. Urinalysis and blood chemistries were within normal limits. Serologies were negative except for cytomegalovirus. The donor had a history of alcohol use, arthritis, and tobacco use (1 pack per day). No chronic medications were listed.

Hepatocytes prepared and pooled from three male and two female donors were obtained from the cryopreserved hepatocyte bank maintained at the study laboratory. Human donor demographics and medical histories are provided as Appendix 1 of this study report. Hepatocytes were isolated and cryopreserved according to previously published methods (2–4). Cryopreserved cells were thawed and counted to determine yield. Viability was measured using Trypan blue exclusion; only cells with greater or equal to 70% viability were used in this study. Suspensions were diluted with substrate media to prepare a 2× cell suspension of $2.0×10^6$ viable cells/mL. Aliquots (0.25 mL) of the 2× hepatocyte suspension were transferred to uncoated 24-well plates, and each well contained $0.5×10^6$ cells in a total final volume of 0.5 mL after the addition of test or control article.

The test article and positive control inhibitors were added to each well as appropriate (wells were pre-labeled according to a sample key), and the samples were preincubated for 15 minutes. After this preincubation, 5 µL of 100× probe substrate stocks were added to the groups as appropriate (wells were pre-labeled according to a sample key), and the samples were incubated for 60 minutes. The following substrates were evaluated: 15 µM phenacetin (CYP1A2), 8 µM coumarin (CYP2A6), 150 µM tolbutamide (CYP2C9), 20 µM S-mephenytoin (CYP2C19), 8 µM dextromethorphan (CYP2D6), 100 µM chlorzoxazone (CYP2E1), and 50 µM testosterone (CYP3A4). Incubation reactions were terminated with the addition of an equal volume of methanol, except for the incubations with phenacetin, which were terminated with the addition of 150 µL acetonitrile; and S-mephenytoin, which were terminated with the addition of 50 µL perchloric acid.

EXAMPLE 5

Control Incubations

Chromatographic Interference Control (CIC)

To investigate the possibility of chromatographic interference by the test article and its metabolites, hepatocytes were incubated with the test article at the highest tested concentration in the absence of substrate for 60 minutes.

Vehicle Control (VC)

To determine activity in the absence of inhibitors and test article, hepatocytes were incubated with substrate media and cosolubilizer.

Positive Control (PC)

To verify the capacity for inhibition by the test system, hepatocytes were preincubated for 15 minutes with chemical inhibitors, then isoform-specific substrates were added to the incubation mixture. PC dosing solutions were prepared to achieve final concentrations of the following known P450 inhibitors: 1 µM furafylline (CYP1A2), 3 µM tranylcypromine (CYP2A6), 10 µM sulfaphenazole (CYP2C9), 25 µM omeprazole (CYP2C19), 2.5 µM quinidine (CYP2D6), 250 µM 4-methylpyrazole (CYP2E1), and 1 µM ketoconazole (CYP3A4).

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention is not limited by the embodiments described above which are presented as examples only but can be modified in various ways within the scope of protection defined by the appended patent claims.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substastially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method of inhibiting cytochrome P450 enzymes selected from the group consisting of CYP1A2, CYP2A6 and CYP3A4, comprising the step of administering an effective inhibition amount of AHT-323A botanical extract to a patient.

2. The method of claim 1, wherein the in vitro $IC_{50}$ value of said AHT-323A botanical extract on said cytochrome P450 enzyme CYP1A2 is about 0.176 mg/ml.

3. The method of claim 1, wherein the in vitro $IC_{50}$ value of said AHT-323A botanical extract on said cytochrome P450 enzyme CYP2A6 is about 0.741 mg/ml.

4. The method of claim 1, wherein the in vitro $IC_{50}$ value of said AHT-323A botanical extract on cytochrome P450 enzyme CYP3A4 is about 0.0366 mg/ml.

* * * * *